US009022917B2

(12) United States Patent
Kasic et al.

(10) Patent No.: US 9,022,917 B2
(45) Date of Patent: May 5, 2015

(54) MAGNETIC SPACER SYSTEMS, DEVICES, COMPONENTS AND METHODS FOR BONE CONDUCTION HEARING AIDS

(71) Applicant: Sophono, Inc., Boulder, CO (US)

(72) Inventors: James F. Kasic, Boulder, CO (US); Nicholas F. Pergola, Arvada, CO (US); Markus C. Haller, Gland (CH)

( * ) Notice: Subject to any disclaimer, the term of this patent is extended or adjusted under 35 U.S.C. 154(b) by 311 days.

(21) Appl. No.: 13/650,057

(22) Filed: Oct. 11, 2012

(65) Prior Publication Data

US 2014/0121451 A1 May 1, 2014

Related U.S. Application Data

(63) Continuation-in-part of application No. 13/550,581, filed on Jul. 16, 2012.

(51) Int. Cl.
*A61F 11/04* (2006.01)
*H04R 25/00* (2006.01)

(52) U.S. Cl.
CPC .......... *H04R 25/606* (2013.01); *H04R 2460/13* (2013.01)

(58) Field of Classification Search
CPC ... H04R 25/606; H04R 2460/13; H04R 3/002
USPC ........................................................... 600/25
See application file for complete search history.

(56) References Cited

U.S. PATENT DOCUMENTS

| | | | |
|---|---|---|---|
| 4,352,960 | A | 10/1982 | Dormer et al. |
| 4,612,915 | A | 9/1986 | Hough et al. |
| 4,726,378 | A | 2/1988 | Kaplan |
| 4,736,747 | A | 4/1988 | Drake |
| RE32,947 | E | 6/1989 | Dormer |
| 4,918,745 | A | 4/1990 | Hutchison |
| 5,558,618 | A | 9/1996 | Maniglia |
| 5,906,635 | A | 5/1999 | Maniglia |
| 6,246,911 | B1 | 6/2001 | Seligman |
| 6,358,281 | B1 | 3/2002 | Berrang et al. |
| 6,517,476 | B1 | 2/2003 | Bedoya et al. |
| 6,537,200 | B2 | 3/2003 | Leysieffer et al. |
| 6,565,503 | B2 | 5/2003 | Leysieffer et al. |
| 6,648,914 | B2 | 11/2003 | Berrang et al. |
| 7,021,676 | B2 | 4/2006 | Westerkull |
| 7,065,223 | B2 | 6/2006 | Westerkull |
| 7,186,211 | B2 | 3/2007 | Schneider et al. |
| 7,386,143 | B2 | 6/2008 | Easter et al. |
| 7,599,508 | B1 | 10/2009 | Lynch et al. |
| 7,856,986 | B2 | 12/2010 | Darley |

(Continued)

OTHER PUBLICATIONS

"A Miniature Bone Vibrator for Hearing Aids and Similar Applications," BHM-Tech Produktiongesellschaft m.b.H, Austria, 2004, Technical Data VKH3391W.

(Continued)

*Primary Examiner* — Christine H Matthews
*Assistant Examiner* — Joshua D Lannu
(74) *Attorney, Agent, or Firm* — Woods Patent Law

(57) ABSTRACT

Various embodiments of systems, devices, components, and methods are disclosed for magnetic spacers configured for use in conjunction with bone conduction hearing aids and corresponding magnetic implants. According to some embodiments, the magnetic spacers are configured to vary the amount and/or orientation or direction of magnetic coupling force provided thereby.

41 Claims, 10 Drawing Sheets

(56) References Cited

U.S. PATENT DOCUMENTS

| | | | |
|---|---|---|---|
| 8,107,661 | B1 | 1/2012 | Lynch et al. |
| 8,170,253 | B1 | 5/2012 | Lynch et al. |
| 8,255,058 | B2 | 8/2012 | Gibson et al. |
| 8,270,647 | B2 | 9/2012 | Crawford et al. |
| 8,315,705 | B2 | 11/2012 | Keuninckx |
| 8,369,959 | B2 | 2/2013 | Meskens |
| 8,452,412 | B2 | 5/2013 | Ibrahim |
| 8,515,112 | B2 | 8/2013 | Crawford et al. |
| 8,538,545 | B2 | 9/2013 | Meskens |
| 8,774,930 | B2 | 7/2014 | Ball |
| 8,787,608 | B2 | 7/2014 | Van Himbeeck et al. |
| 8,811,643 | B2 | 8/2014 | Crawford et al. |
| 8,891,795 | B2 | 11/2014 | Andersson |
| 8,897,475 | B2 | 11/2014 | Ball et al. |
| 8,897,883 | B2 | 11/2014 | Griffith |
| 8,923,968 | B2 | 12/2014 | Meskens |
| 8,934,984 | B2 | 1/2015 | Meskens et al. |
| 2004/0210103 | A1* | 10/2004 | Westerkull ...................... 600/25 |
| 2007/0053536 | A1 | 3/2007 | Westerkull |
| 2007/0274551 | A1 | 11/2007 | Tsai et al. |
| 2009/0248155 | A1 | 10/2009 | Parker |
| 2009/0299437 | A1 | 12/2009 | Zimmerling |
| 2010/0145135 | A1 | 6/2010 | Ball et al. |
| 2011/0022120 | A1 | 1/2011 | Ball et al. |
| 2011/0216927 | A1 | 9/2011 | Ball |
| 2012/0029267 | A1 | 2/2012 | Ball |
| 2012/0041515 | A1 | 2/2012 | Meskens et al. |
| 2012/0088957 | A1 | 4/2012 | Adamson et al. |
| 2012/0238799 | A1 | 9/2012 | Ball et al. |
| 2012/0296155 | A1 | 11/2012 | Ball |
| 2012/0302823 | A1 | 11/2012 | Andersson et al. |
| 2013/0018218 | A1 | 1/2013 | Haller et al. |
| 2013/0046131 | A1 | 2/2013 | Ball et al. |
| 2013/0261377 | A1 | 10/2013 | Adamson et al. |
| 2013/0281764 | A1 | 10/2013 | Goeran et al. |
| 2014/0121447 | A1 | 5/2014 | Kasic et al. |
| 2014/0121449 | A1 | 5/2014 | Kasic et al. |
| 2014/0121450 | A1 | 5/2014 | Kasic et al. |
| 2014/0121451 | A1 | 5/2014 | Kasic et al. |
| 2014/0121452 | A1 | 5/2014 | Kasic et al. |
| 2014/0193011 | A1 | 7/2014 | Parker |
| 2014/0270293 | A1 | 9/2014 | Ruppersberg et al. |
| 2014/0275735 | A1 | 9/2014 | Ruppersberg et al. |
| 2014/0275736 | A1 | 9/2014 | Ruppersberg et al. |
| 2014/0336447 | A1 | 11/2014 | Bjom et al. |
| 2015/0016649 | A1 | 1/2015 | Van Himbeeck et al. |

OTHER PUBLICATIONS

"Microphone 8010T", Data Sheet, RoHS, Sonion, Dec. 20, 2007.

"Inspiria Extreme Digital DSP System," Preliminary Data Sheet, Sound Design Technologies, Mar. 2009.

"Alpha I (S) & Alpha I (M) Bone Conduction Hearing Systems," Physician Manual, Sophono.

* cited by examiner

ALPHA 1

BAHA

AUDIANT
(PRIOR ART)

MAGNETIC SPACER SYSTEMS, DEVICES, COMPONENTS AND METHODS FOR BONE CONDUCTION HEARING AIDS

RELATED APPLICATIONS

This application is a continuation-in-part of, and claims priority and other benefits from, U.S. patent application Ser. No. 13/550,581 entitled "Systems, Devices, Components and Methods for Bone Conduction Hearing Aids" to Pergola et al. filed Jul. 16, 2012 (hereafter "the '581 patent application"). The '581 patent application is hereby incorporated by reference herein, in its entirety.

This application also hereby incorporates by reference, each in its respective entirety, the following patent applications filed on even date herewith: (1) U.S. patent application Ser. No. 13/649,934 entitled "Adjustable Magnetic Systems, Devices, Components and Methods for Bone Conduction Hearing Aids" to Kasic et al.; (2) U.S. patent application Ser. No. 13/650,026 entitled "Magnetic Abutment Systems, Devices, Components and Methods for Bone Conduction Hearing Aids" to Kasic et al., and (3) U.S. patent application Ser. No. 13/650,080 entitled "Abutment Attachment Systems, Mechanisms, Devices, Components and Methods for Bone Conduction Hearing Aids" to Kasic et al.

FIELD OF THE INVENTION

Various embodiments of the invention described herein relate to the field of systems, devices, components, and methods for bone conduction hearing aid devices.

BACKGROUND

A magnetic bone conduction hearing aid is held in position on a patient's head by means of magnetic attraction that occurs between magnetic members included in the hearing aid and magnetic members included in a magnetic implant that has been implanted beneath the patient's skin, and that has been affixed to the patient's skull. If a patient's skin or tissue at such a single location is particularly thin or becomes irritated or inflamed while the magnetic hearing aid is being worn, or if the patent is uncomfortable, or experiences discomfort or pain when wearing the hearing aid, then the only effective remedy for the pain or discomfort may be to remove the magnetic hearing aid from the patient's head. In addition, a magnetic bone conduction hearing aid must possess sufficient magnetic coupling capability to remain secured to a patient's skull during everyday use.

Many patients wearing magnetically-coupled hearing aids regularly experience episodes of accelerative forces caused, for example, by patients hopping, jumping or being jarred. Magnetic bone conduction hearing aids must therefore possess sufficient magnetic coupling forces to withstand such forces and yet remain attached to the patient's skull. On the other hand, magnetic coupling forces provided by magnetic bone conduction hearing aids cannot be excessive, for otherwise tissue necrosis or ischemia can develop in the tissue underlying magnetic spacer.

Skull bone geometries, tissue thicknesses, patient susceptibility to pain or discomfort, and magnetic implant positions also vary from patient to patient.

The above factors complicate comfortable, effective and suitable or sufficiently strong magnetic coupling of magnetic bone conduction hearing aids to patient's skulls.

What is needed is a magnetic bone conduction hearing aid and corresponding magnetic implant that permit a hearing aid to be positioned comfortably on a chronic basis on a variety of different patients' skulls.

SUMMARY

In one embodiment, there is provided a magnetic hearing device comprising at least one housing, an electromagnetic ("EM") transducer disposed within or attached to the housing, and a magnetic spacer comprising at least one magnetic member, the magnetic spacer being configured to be: (i) mechanically and acoustically coupled to the EM transducer, and (ii) magnetically coupled to an implantable member through a patient's skin, wherein the magnetic spacer is further configured such that at least one of: (a) a user may remove and replace the magnetic member from the magnetic spacer; (b) the user may add or remove at least one additional magnetic member to or from the magnetic spacer; (c) a user may remove the magnetic spacer from the device and replace it with a different magnetic spacer or with changes to the magnetic spacer; (d) the user may adjust a position of the magnetic member in the magnetic spacer so as to change or adjust a degree of magnetic coupling of the magnetic spacer to the implantable member; (e) the user may adjust a position of the magnetic member so as to change or adjust relative positioning or spacing between the magnetic spacer and the implantable member; (f) at least a portion of the magnetic spacer is custom shaped to conform with skull contours underlying a desired skin contact region of a given patient; (g) at least a portion of the magnetic spacer is configured to be conformable with skull contours underlying the desired skin contact region of the given patient, and (h) at least portions of the magnetic member are shaped and configured for placement near a periphery of the magnetic spacer so as to permit a reduction in a thickness of the magnetic spacer between at least portions of the EM transducer and the patient's skin.

In another embodiment, there is provided a magnetic spacer configured for use in conjunction with a hearing device, the hearing device comprising at least one housing and an electromagnetic ("EM") transducer disposed within or attached to the housing, the magnetic spacer comprising at least one magnetic member, the magnetic spacer being configured to be: (i) mechanically and acoustically coupled to the EM transducer, and (ii) magnetically coupled to an implantable member through a patient's skin, wherein the magnetic spacer is further configured such that at least one of: (a) a user may remove and replace the magnetic member from the magnetic spacer; (b) the user may add or remove at least one additional magnetic member to the magnetic spacer; (c) a user may remove the magnetic spacer from the device and replace it with a different magnetic spacer or with changes to the magnetic spacer; (d) the user may adjust a position of the magnetic member in the magnetic spacer so as to change or adjust a degree of magnetic coupling of the magnetic spacer to the implantable member; (e) the user can adjust a position of the magnetic member so as to change or adjust relative positioning or spacing between the magnetic spacer and the implantable member; (f) at least a portion of the magnetic spacer is custom shaped to conform with skull contours underlying a desired skin contact region of a given patient; (g) at least a portion of the magnetic spacer is configured to be conformable with skull contours underlying the desired skin contact region of the given patient, and (h) at least portions of the magnetic member are shaped and configured for placement near a periphery of the magnetic spacer so as to permit a reduction in a thickness of the magnetic spacer between at least portions of the EM transducer and the patient's skin.

In yet another embodiment, there is provided a method of adjusting a fit or coupling of a magnetic hearing device to a patient's head, the device comprising at least one housing, an electromagnetic ("EM") transducer disposed within or attached to the housing, and a magnetic spacer comprising at least one magnetic member, the magnetic spacer configured to be mechanically and acoustically coupled to the EM transducer, and further being configured to be magnetically coupled to an implantable member through the patient's skin, the method comprising at least one of: (a) a user removing and replacing the magnetic member from the magnetic spacer; (b) the user adding or removing at least one additional magnetic member to the magnetic spacer; (c) the user removing the magnetic spacer from the device and replacing it with a different magnetic spacer or with changes to the magnetic spacer; (d) the user adjusting a position of the magnetic member in the magnetic spacer so as to change or adjust a degree of magnetic coupling of the magnetic spacer to the implantable member; (e) the user adjusting a position of the magnetic member so as to change or adjust relative positioning or spacing between the magnetic spacer and the implantable member, and (f) conforming at least a portion of the magnetic spacer with skull contours underlying a desired skin contact region of a given patient.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

FIG. 2(*b*) shows one embodiment of a prior art wiring diagram for a SOPHONO ALPHA 1 hearing aid manufactured using an SA3286 DSP;

FIG. 3(*b*) shows one embodiment of a prior art SOPHONO® ALPHA 1® hearing aid 10;

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for bone conduction and/or bone-anchored hearing aids.

A bone-anchored hearing device (or "BAHD") is an auditory prosthetic device based on bone conduction having a portion or portions thereof which are surgically implanted. A BAHD uses the bones of the skull as pathways for sound to travel to a patient's inner ear. For people with conductive hearing loss, a BAHD bypasses the external auditory canal and middle ear, and stimulates the still-functioning cochlea via an implanted metal post. For patients with unilateral hearing loss, a BAHD uses the skull to conduct the sound from the deaf side to the side with the functioning cochlea. In most BAHA systems, a titanium post or plate is surgically embedded into the skull with a small abutment extending through and exposed outside the patient's skin. A BAHD sound processor attaches to the abutment and transmits sound vibrations through the external abutment to the implant. The implant vibrates the skull and inner ear, which stimulates the nerve fibers of the inner ear, allowing hearing. A BAHD device can also be connected to an FM system or iPod by means of attaching a miniaturized FM receiver or Bluetooth connection thereto.

BAHD devices manufactured by COCHLEAR™ of Sydney, Australia, and OPTICON™ of Smoerum, Sweden. SOPHONO™ of Boulder, Colo. manufactures an Alpha 1 magnetic hearing aid device, which attaches by magnetic means behind a patient's ear to the patient's skull by coupling to a magnetic or magnetized bone plate (or "magnetic implant") implanted in the patient's skull beneath the skin.

Surgical procedures for implanting such posts or plates are relatively straightforward, and are well known to those skilled in the art. See, for example, "Alpha I (S) & Alpha I (M) Physician Manual—REV A S0300-00" published by Sophono, Inc. of Boulder, Colo., the entirety of which is hereby incorporated by reference herein.

Figures 1A, 1B, 1C:
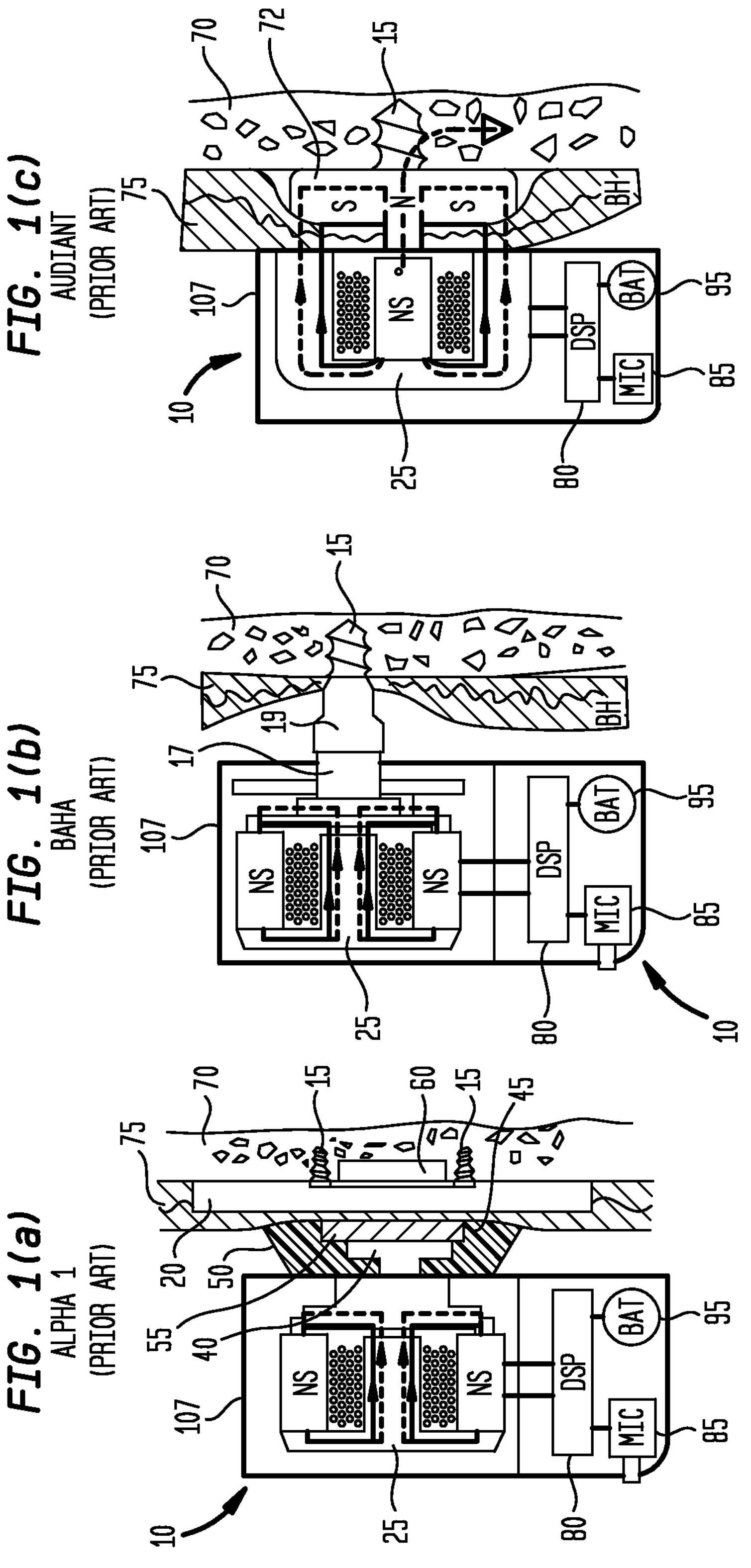
(PRIOR ART) FIG. 1(b)
(PRIOR ART) FIG. 1(c)
FIGS. 1(*a*), 1(*b*) and 1(*c*) show side cross-sectional schematic views of selected embodiments of prior art SOPHONO ALPHA 1, BAHA and AUDIANT bone conduction hearing aids, respectively.

FIGS. 1(*a*), 1(*b*) and 1(*c*) show side cross-sectional schematic views of selected embodiments of prior art SOPHONO ALPHA 1, BAHA and AUDIANT bone conduction hearing aids, respectively. Note that FIGS. 1(*a*), 1(*b*) and 1(*c*) are not necessarily to scale.

In FIG. 1(*a*), magnetic hearing aid device 10 comprises housing 107, electromagnetic/bone conduction ("EM") transducer 25 with corresponding magnets and coils, digital signal processor ("DSP") 80, battery 95, magnetic spacer 50, magnetic implant or magnetic implant bone plate 20. As shown in FIGS. 1(*a*) and 2(*a*), and according to one embodiment, magnetic implant 20 comprises a frame 21 (see FIG. 3(*a*)) formed of a biocompatible metal such as medical grade titanium that is configured to have disposed therein or have attached thereto implantable magnets or magnetic members 60. Bone screws 15 secure or affix magnetic implant 20 to skull 70, and are disposed through screw holes 22 of frame 21 (see FIG. 2(*a*)). Magnetic members 60 are configured to couple magnetically to one or more corresponding external magnetic members or magnets 55 mounted onto or into, or otherwise forming a portion of, magnetic spacer 50, which in turn is operably coupled to EM transducer 25 and metal disc 40. DSP 80 is configured to drive EM transducer 25, metal disk 40 and magnetic spacer 50 in accordance with external audio signals picked up by microphone 85. DSP 80 and EM transducer 25 are powered by battery 95, which according to one embodiment may be a zinc-air battery, or may be any other suitable type of primary or secondary (i.e., rechargeable) electrochemical cell such as an alkaline or lithium battery.

As further shown in FIG. 1(*a*), magnetic implant 20 is attached to patient's skull 70, and is separated from magnetic spacer 50 by patient's skin 75. Hearing aid device 10 of FIG. 1(*a*) is thereby operably coupled magnetically and mechanically to plate 20 implanted in patient's skull 70, which permits the transmission of audio signals originating in DSP 80 and EM transducer 25 to the patient's inner ear via skull 70.

FIG. 1(*b*) shows another embodiment of hearing aid 10, which is a BAHA® device comprising housing 107, EM transducer 25 with corresponding magnets and coils, DSP 80, battery 95, external post 17, internal bone anchor 115, and abutment member 19. In one embodiment, and as shown in FIG. 1(*b*), internal bone anchor 115 includes a bone screw formed of a biocompatible metal such as titanium that is configured to have disposed thereon or have attached thereto abutment member 19, which in turn may be configured to mate mechanically or magnetically with external post 17, which in turn is operably coupled to EM transducer 25. DSP 80 is configured to drive EM transducer 25 and external post 17 in accordance with external audio signals picked up by microphone 85. DSP 80 and EM transducer 25 are powered by battery 95, which according to one embodiment is a zinc-air battery (or any other suitable battery or electrochemical cell as described above). As shown in FIG. 1(*b*), implantable bone anchor 115 is attached to patient's skull 70, and is also attached to external post 17 through abutment member 19, either mechanically or by magnetic means. Hearing aid device 10 of FIG. 1(*b*) is thus coupled magnetically and/or mechanically to bone anchor 15 implanted in patient's skull 70, thereby permitting the transmission of audio signals originating in DSP 80 and EM transducer 25 to the patient's inner ear via skull 70.

FIG. 1(*c*) shows another embodiment of hearing aid 10, which is an AUDIANT®-type device, where an implantable magnetic member 72 is attached by means of bone anchor 115 to patient's skull 70. Internal bone anchor 115 includes a bone screw formed of a biocompatible metal such as titanium, and has disposed thereon or attached thereto implantable magnetic member 72, which couples magnetically through patient's skin 75 to EM transducer 25. DSP 80 is configured to drive EM transducer 25 in accordance with external audio signals picked up by microphone 85. Hearing aid device 10 of FIG. 1(*c*) is thus coupled magnetically to bone anchor 15 implanted in patient's skull 70, thereby permitting the transmission of audio signals originating in DSP 80 and EM transducer 25 to the patient's inner ear via skull 70.

Figure 2A:
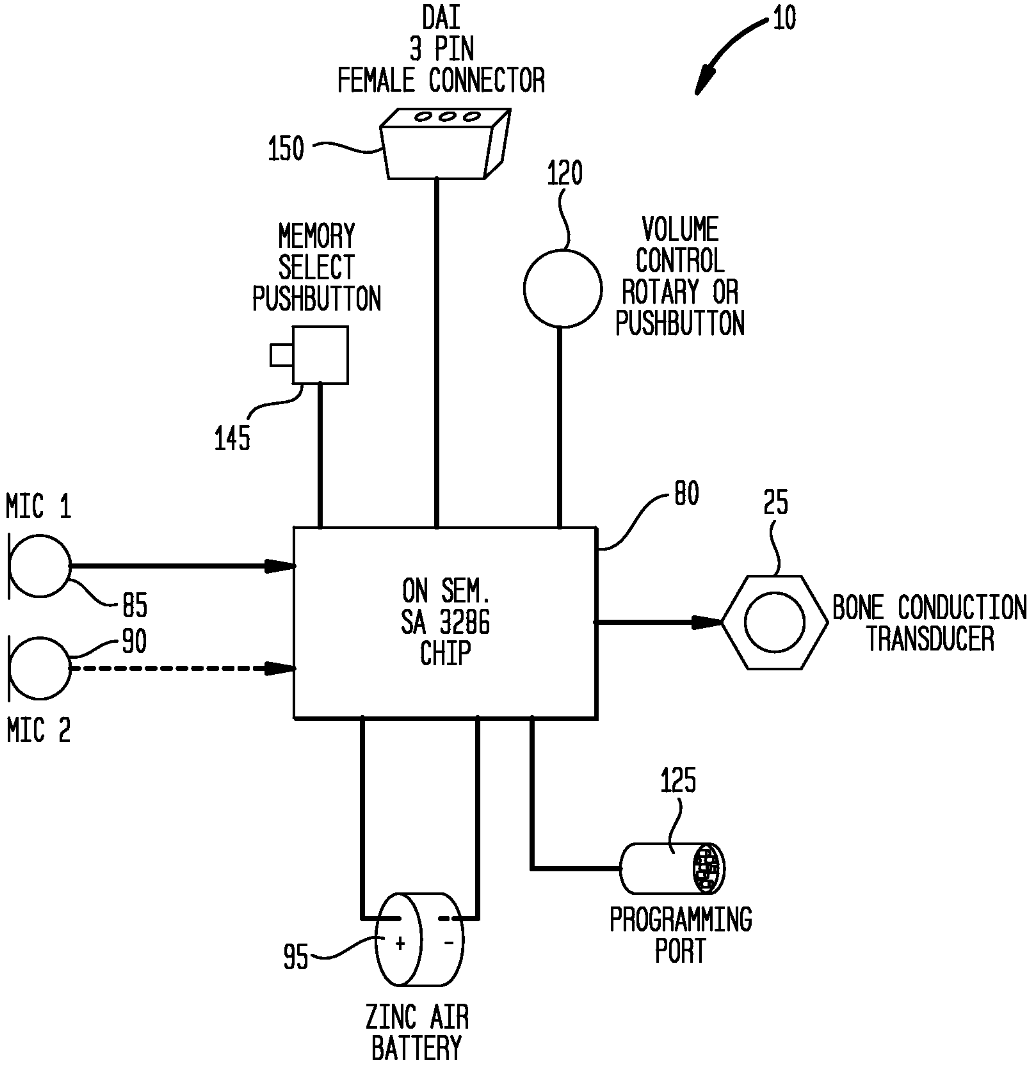
FIG. 2(a) (PRIOR ART)
FIG. 2(*a*) shows one embodiment of a prior art functional electronic and electrical block diagram of hearing aid 10 shown in FIGS. 1(*a*) and 3(*b*)
Figure 2B:
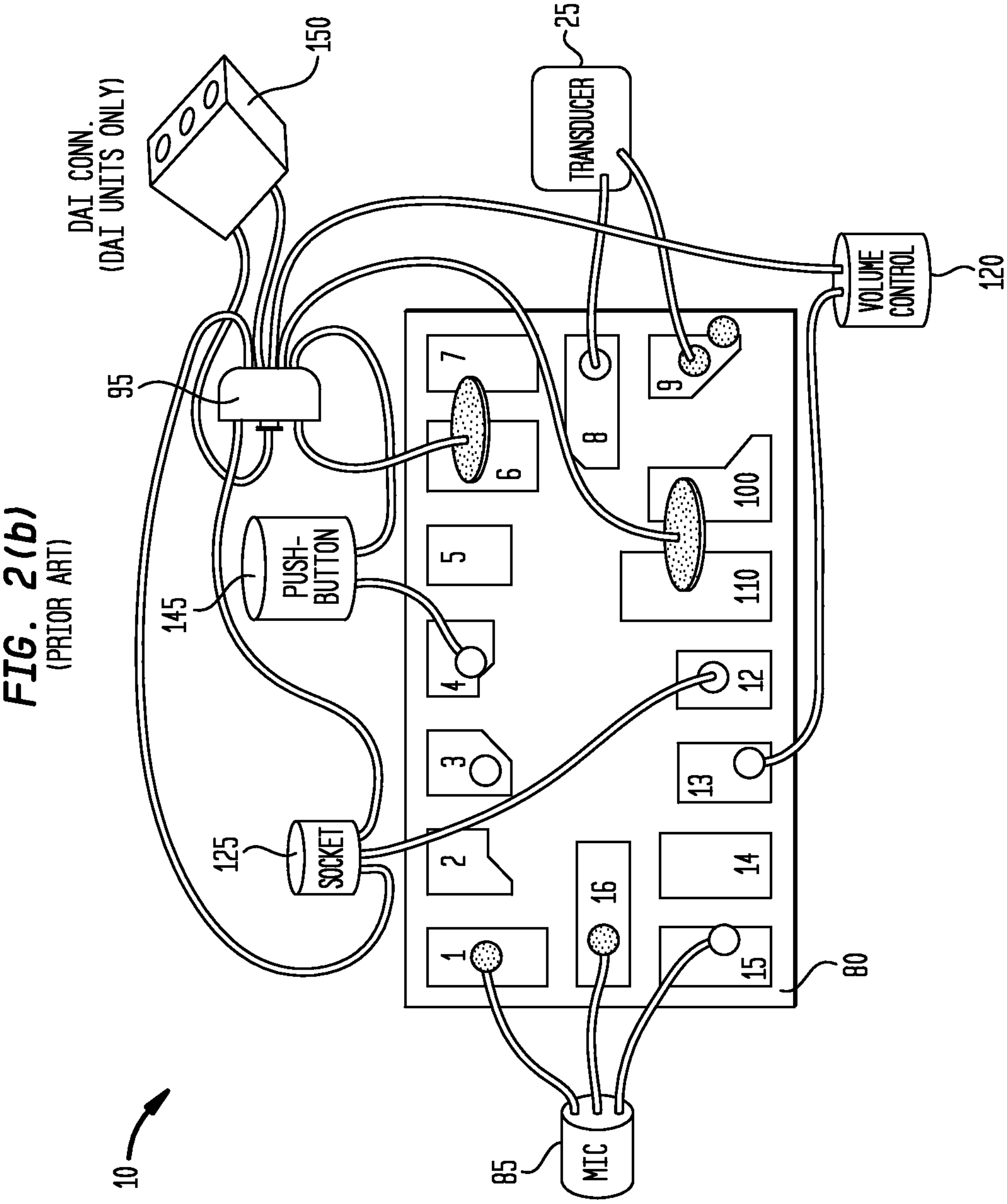
FIG. 2(b) (PRIOR ART)

FIG. 2(*a*) shows one embodiment of a prior art functional electronic and electrical block diagram of hearing aid 10 shown in FIGS. 1(*a*) and 2(*b*). In the block diagram of FIG. 2(*a*), and according to one embodiment, DSP 80 is a SOUND DESIGN TECHNOLOGIES® SA3286 INSPIRA EXTREME® DIGITAL DSP, for which data sheet 48550-2 dated March 2009, filed on even date herewith in an accompanying Information Disclosure Statement ("IDS"), is hereby incorporated by reference herein in its entirety. The audio processor for the SOPHONO ALPHA 1 hearing aid is centered around DSP chip 80, which provides programmable signal processing. The signal processing may be customized by computer software which communicates with the Alpha through programming port 125. According to one embodiment, the system is powered by a standard zinc air battery 95 (i.e. hearing aid battery), although other types of batteries may be employed. The SOPHONO ALPHA 1 hearing aid detects acoustic signals using a miniature microphone 85. A second microphone 90 may also be employed, as shown in FIG. 2(*a*). The SA 3286 chip supports directional audio processing with second microphone 90 to enable directional processing. Direct Audio Input (DAI) connector 150 allows connection of accessories which provide an audio signal in addition to or in lieu of the microphone signal. The most common usage of the DAI connector is FM systems. The FM receiver may be plugged into DAI connector 150. Such an FM transmitter can be worn, for example, by a teacher in a classroom to ensure the teacher is heard clearly by a student wearing hearing aid 10. Other DAI accessories include an adapter for a music player, a telecoil, or a Bluetooth phone accessory. According to one embodiment, DSP 80 or SA 3286 has 4 available program memories, allowing a hearing health professional to customize each of 4 programs for different listening situations. The Memory Select Pushbutton 145 allows the user to choose from the activated memories. This might include special frequency adjustments for noisy situations, or a program which is Directional, or a program which uses the DAI input.

FIG. 2(*b*) shows one embodiment of a prior art wiring diagram for a SOPHONO ALPHA 1 hearing aid manufactured using the foregoing SA3286 DSP. Note that the various embodiments of hearing aid 10 are not limited to the use of a SA3286 DSP, and that any other suitable CPU, processor, controller or computing device may be used. According to one embodiment, DSP 80 is mounted on a printed circuit board 155 disposed within housing 110 and/or housing 115 of hearing aid 10 (not shown in the Figures).

In some embodiments, the microphone incorporated into hearing aid 10 is an 8010T microphone manufactured by SONION®, for which data sheet 3800-3016007, Version 1 dated December, 2007, filed on even date herewith in the accompanying IDS, is hereby incorporated by reference herein in its entirety. Other suitable types of microphones, including other types of capacitive microphones, may be employed.

In still further embodiments, the electromagnetic transducer 25 incorporated into hearing aid 10 is a VKH3391W transducer manufactured by BMH-Tech® of Austria, for which the data sheet filed on even date herewith in the accompanying IDS is hereby incorporated by reference herein in its entirety. Other types of suitable EM transducers may also be used.

Figure 3A:
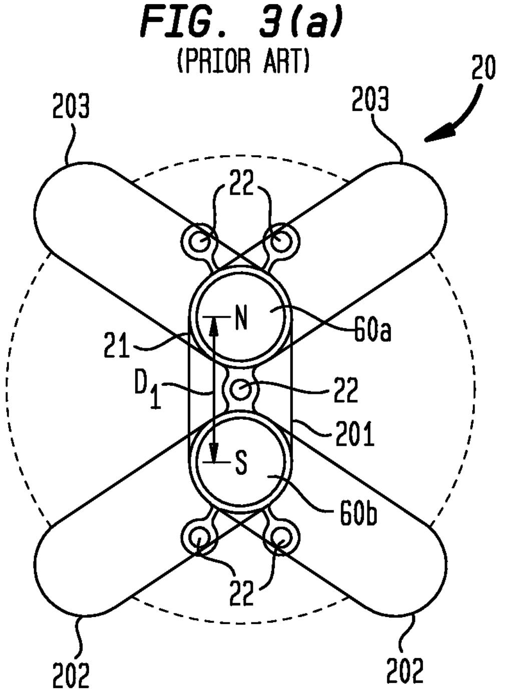
FIG. 3(a) (PRIOR ART)
FIG. 3(*a*) shows one embodiment of prior art magnetic implant 20 according to FIG. 1(*a*), and various positions that overlying magnetic spacer 50 may assume in respect thereof.
Figure 3B:
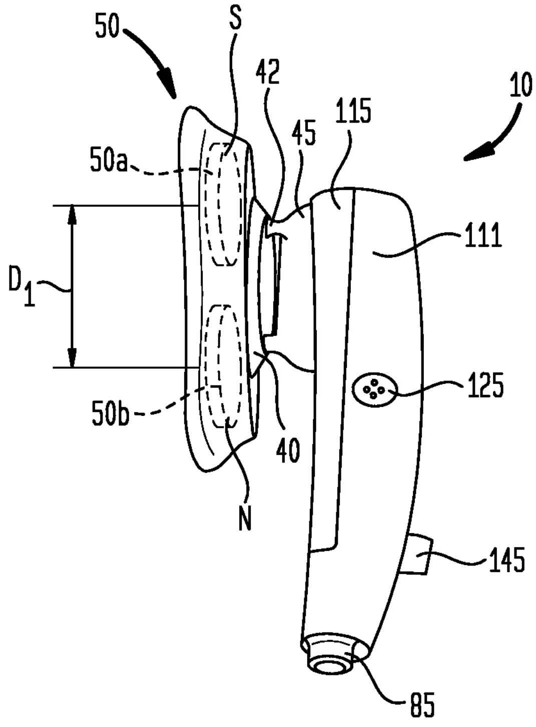
FIG. 3(b) (PRIOR ART)

FIGS. 3(*a*) and 3(*b*) show implantable bone plate or magnetic implant 20 in accordance with FIG. 1(*a*), where frame 22 has disposed thereon or therein magnetic members **60*a* and 60*b*, and where magnetic spacer 50 of hearing aid 10 has magnetic members 55*a* and 55*b* spacer disposed therein. The two magnets 60*a* and 60*b* of magnetic implant 20 of FIG. 2**(*a*) permit hearing aid 10 and magnetic spacer 50 to be placed in a single position on patient's skull 70, with respective opposing north and south poles of magnetic members **55*a*, 60*a*, 55*b* and 60*b* appropriately aligned with respect to one another to permit a sufficient degree of magnetic coupling to be achieved between magnetic spacer 50 and magnetic implant 20 (see also FIG. 3**(*b*)). As shown in FIG. 1(*a*), magnetic implant 20 is preferably configured to be affixed to skull 70 under patient's skin 75. In one aspect, affixation of magnetic implant 20 to skull 75 is by direct means, such as by screws 15. Other means of attachment known to those skilled in the art are also contemplated, however, such as glue, epoxy, and sutures.

Referring now to FIG. 3(*b*), there is shown a SOPHONO® ALPHA 1® hearing aid 10 configured to operate in accordance with magnetic implant 20 of FIG. 3(*a*). As shown, hearing aid 10 of FIG. 3(*b*) comprises upper housing 111, lower housing 115, magnetic spacer 50, external magnets **55*a* and 55*b* disposed within spacer 50, EM transducer diaphragm 45, metal disk 40 connecting EM transducer 25 to spacer 50, programming port/socket 125, program switch 145, and microphone 85. Not shown in FIG. 3**(*b*) are other aspects of the embodiment of hearing aid 10, such as volume control 120, battery compartment 130, battery door 135, battery contacts 140, direct audio input (DAI) 150, and hearing aid circuit board 155 upon which various components are mounted, such as DSP 80.

Continuing to refer to FIGS. 3(*a*) and 3(*b*), frame 22 of magnetic implant 20 holds a pair of magnets 60*a* and 60*b* that correspond to magnets 55*a* and 55*b* included in spacer 50 shown in FIG. 3(*b*). The south (S) pole and north (N) poles of magnets 55*a* and 55*b*, are respectively configured in spacer 50 such that the south pole of magnet 55*a* is intended to overlie and magnetically couple to the north pole of magnet 60*a*, and such that the north pole of magnet 55*b* is intended to overlie and magnetically couple to the south pole of magnet 60*b*. This arrangement and configuration of magnets 55*a*, 55*b*, 60*a* and 60*b* is intended permit the magnetic forces required to hold hearing aid 10 onto a patient's head to be spread out or dispersed over a relatively wide surface area of the patient's hair and/or skin 75, and thereby prevent irritation of soreness that might otherwise occur if such magnetic forces were spread out over a smaller or more narrow surface area.

Figure 4:
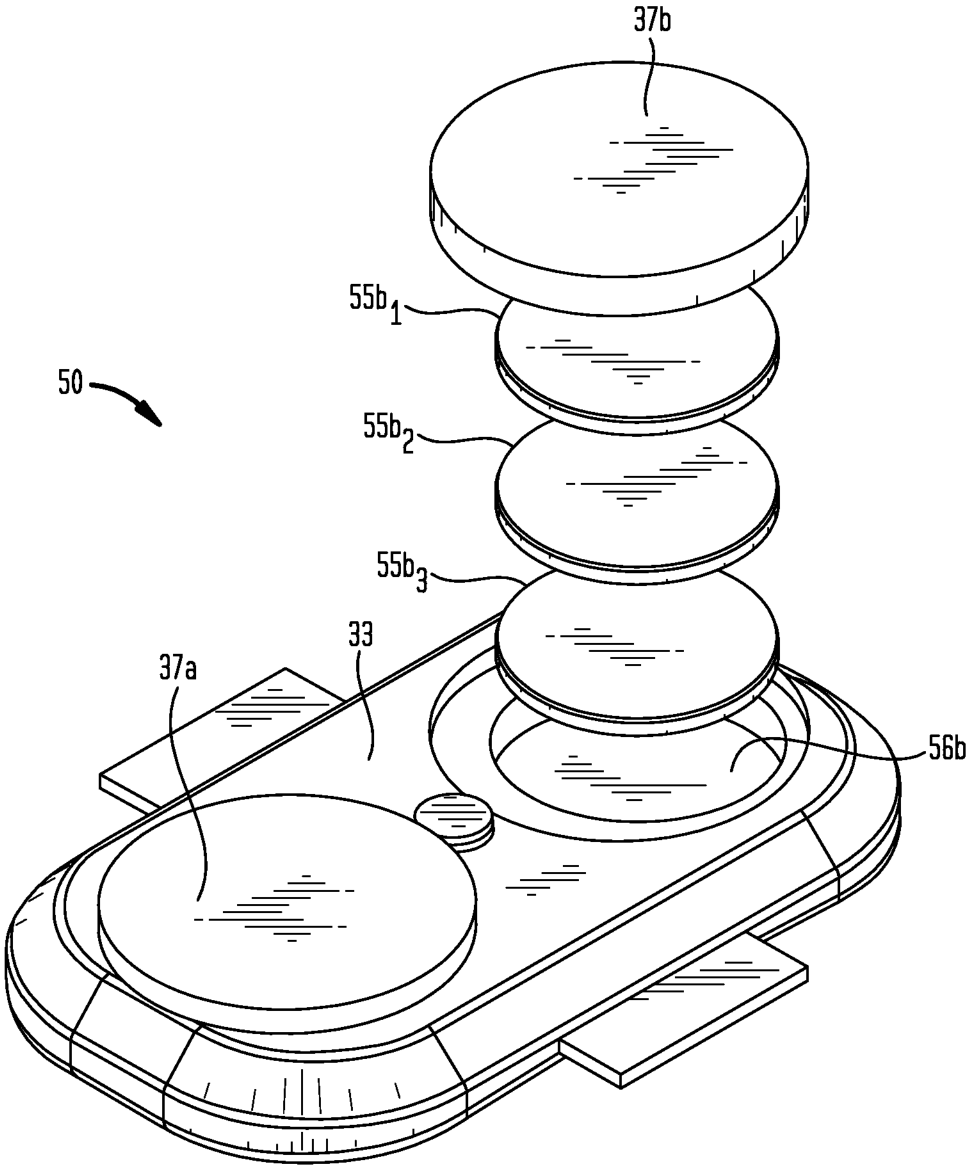
FIG. 4 shows a top perspective view of one embodiment of magnetic spacer 50 with multiple stacked magnet members.

FIG. 4 shows a top perspective view of one embodiment of magnetic spacer 50 comprising multiple stacked magnet members 55*b*$_1$, 55*b*$_2$ and 55*b*$_3$, which are disposed in recess 56*b*. Corresponding stacked magnet members 55*a*$_1$, 55*a*$_2$ and 55*a*$_3$ are disposed beneath cap 37*a*. Cap 37*b* is configured to secure multiple stacked magnet members 55*b*$_1$, 55*b*$_2$ and 55*b*$_3$ within magnetic spacer 50, and may be configured to be screwed onto or otherwise attached to top surface 33 of magnetic spacer 50, or to portions of the sidewalls of recess 56*b*.

According to one embodiment, and continuing to refer to FIG. 4, the total magnetic coupling, pull or adhesion force provided by magnetic spacer 50 may be adjusted by selecting magnetic members 55*a*$_1$, 55*a*$_2$ and 55*a*$_3$ such that together they provide a desired total amount of magnetic force. Thus, some of the selected magnetic members 55*a*$_1$, 55*a*$_2$ and 55*a*$_3$ may exhibit reduced magnetic forces, while others of selected magnetic members 55*a*$_1$, 55*a*$_2$ and 55*a*$_3$ may exhibit increased magnetic forces. For example, the magnetic pull forces provided by each of magnetic members 55*a*$_1$, 55*a*$_2$ and 55*a*$_3$ may be varied by selecting magnetic members having different thicknesses, different diameters, different magnetic materials, different amounts of magnetic materials contained therein, or by using dummy spacers that provide little or no magnetic pull force. In such a manner, a customized total amount of magnetic force provided by magnetic spacer may be furnished according to a patient's particular needs and requirements. The amount of force provided by each stack of magnetic members 55*a*$_1$, 55*a*$_2$ and 55*a*$_3$, and 55*b*$_1$, 55*b*$_2$ and 55*b*$_3$, may also be varied.

Continuing to refer to FIG. 4, it will now be seen that the amount of magnetic coupling force provided by magnetic spacer 50 when spacer 50 is operably mounted over magnetic implant 20 may be adjusted and customized by a patient and/or health care provider according to the pain, discomfort, irritation, skin thickness, skull bone geometry and magnetic implant 20 implantation position characteristics of a given patient. Moreover, the amount of magnetic coupling force provided by each side of magnetic spacer 50 (i.e., one side of magnetic spacer 50 represented by first stack of magnetic members 55*a*$_1$, 55*a*$_2$ and 55*a*$_3$, and another side of magnetic spacer 50 represented by second stack of 55*b*$_1$, 55*b*$_2$ and 55*b*$_3$) may be modulated or adjusted to provide more or less magnetic coupling force on one side of magnetic spacer 50 with respect to the other side of magnetic spacer 50. Such adjustments of magnetic coupling force may be tuned according to each patient's requirements and characteristics, and moreover may be changed for the same patient over time with changing states of patient pain, discomfort, irritation, magnetic coupling, bone growth or necrosis, and so on. According to one embodiment, the magnetic coupling forces of magnetic spacer 50 are adjusted and/or customized when the patient is initially fitted with magnetic spacer and hearing aid 10. During follow-up visits to the health care provider, further adjustments and/or customization of such magnetic coupling forces may be carried out as necessary.

FIGS. 5 through 19 show various embodiments of magnetic spacers 50 for use in conjunction with magnetically coupled hearing device 10 and magnetic implant 20. The embodiments of spacers 50 shown in FIGS. 5 through 19 are configured to permit the amount of magnetic coupling force provided by magnetic spacer 50 to be adjusted and customized by a patient and/or health care provider, as described above. In some embodiments, magnetic spacers 50 are specially contoured for better contact with patient's skin or tissue 75, particularly in the region of the skull shape underlying the desired skin contact region. In other embodiments, magnetic spacer 50 is positioned over skin 75. In still other embodiments, magnetic spacer 50 is positioned under skin 75. In yet other embodiments, magnetic spacer 50 has a low profile. In some embodiments magnetic spacer 50 has low profile characteristics and is custom-contoured to patient's skin 75 (e.g., the skull shape underlying the desired skin contact region). The spacing of magnetic members 55 from the surface of skull 70 may be variable, allowing adjustment of the magnetic retention force by adjusting the spacing of magnets 55. Still further embodiments of magnetic spacer 50 are provided that permit the amount, direction and/or orientation of magnetic coupling forces provided thereby to be adjusted, more about which is said below.

Figure 5:
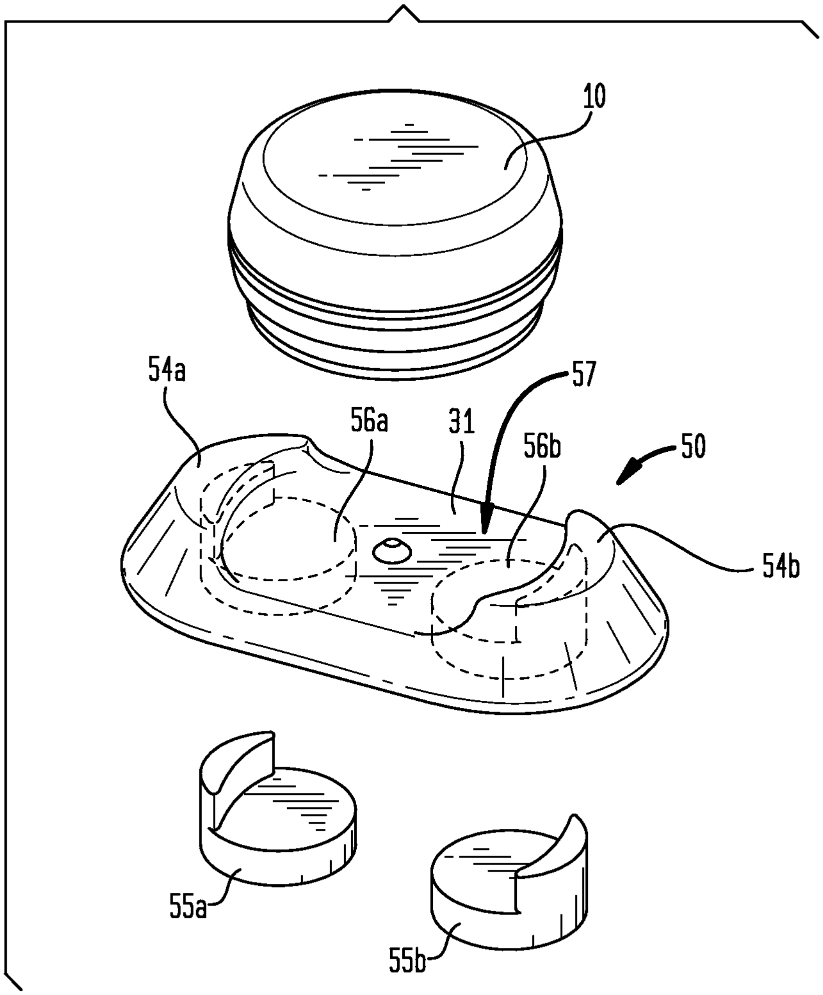
FIGS. 5 through 19 show various embodiments of magnetic spacers 50 for use in conjunction with magnetically coupled hearing device 10 and magnetic implant 20.
Figure 6:
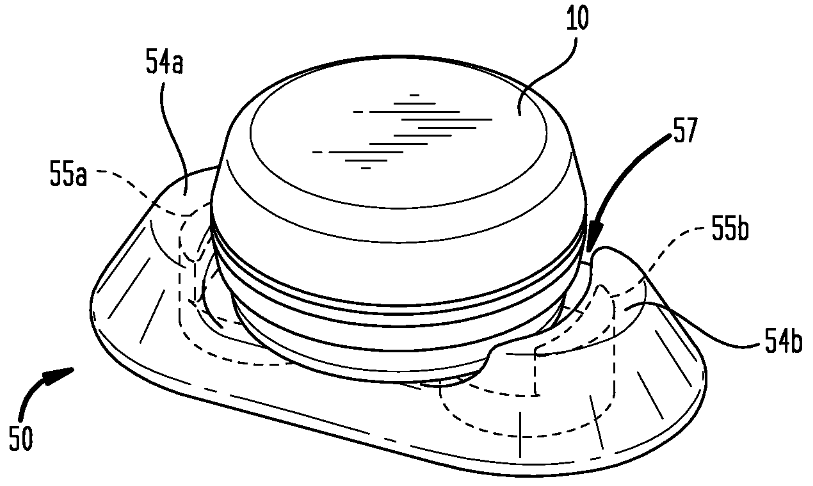
Figure 7:
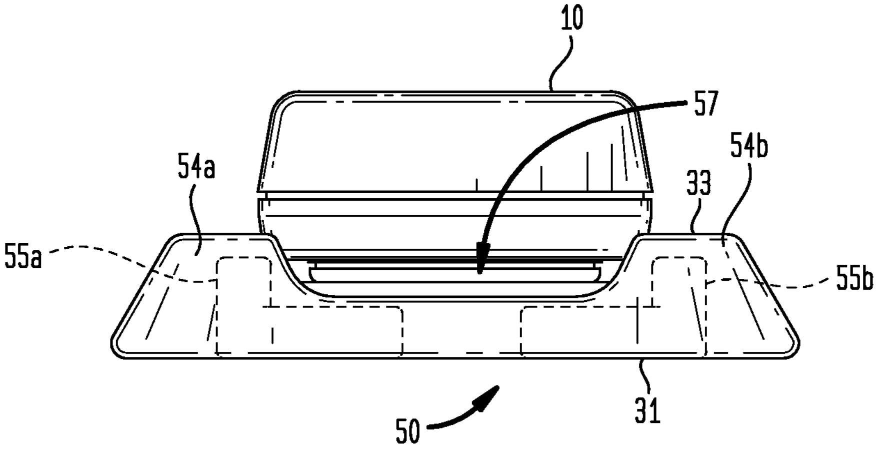
Figure 8:
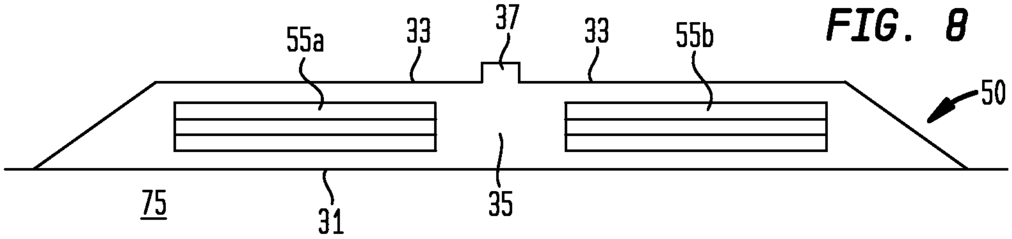

Referring now to FIGS. 5, 6 and 7, there is shown one embodiment of a low-profile magnetic spacer 50. For cosmetic and safety reasons it is important to keep hearing device 10 in as low a profile as possible against the side of the patient's head. However, if multiple magnetic members required to provide increased holding strength, then hearing aid device 10 may become correspondingly larger and farther away from the patient's skull 70. FIGS. 5, 6 and 7 show one embodiment where hearing aid device 10 is configured to be received in central portions or recesses 56*a* and 56*b* of magnetic spacer 50, and where magnetic spacer 50 is configured to receive magnets 55*a* and 55*b* at either end thereof. Shaped magnets 55*a* and 55*b* are configured to fit within the outer shoulders 54*a* and 54*b* of magnetic spacer 50, which sit above the lowermost portions of magnetic spacer 50, thereby conserving valuable volume and permitting device 10 to be placed as close as possible to patient's skin 70 and skull 75. Magnetic spacer 50 features recess 57 for device 10, and uses shaped magnets 55*a* and 55*b* around the periphery thereof for increased holding strength without decreasing the profile of hearing aid device 10 when used by the patient.

In other embodiments, magnetic spacers 50 featuring variable thickness are provided. The thickness of skin 75 over a temporal bone can vary from less than 2 mm to over 8 mm, which can significantly affect the retention or magnetic coupling force created between implanted and external magnets 60 and 55. Additionally, a given patient may desire variable retention force to accommodate different activities (e.g., a child might use a lower retention force during class but a stronger retention force during play time). A number of different embodiments of magnetic spacer 50 are disclosed herein that permit variation of the distance between magnetic members 55*a* and 55*b* (or corresponding stacks of magnetic members) of magnetic spacer 50 and the surface of the patient's head, or that otherwise permit the amount of magnetic coupling force provided by magnetic spacer 50 to be adjusted or changed.

FIGS. 8 through 12 show various embodiments of magnetic spacers 50 that permit variation of the distance between magnets 55*a* and 55*b* ((or corresponding stacks of magnetic members) and skin 75. In an embodiment shown in FIG. 8, a "standard" magnetic spacer 50 with stacks of magnet members 55*a* and 55*b* is embedded in a rigid material. However, different such "standard" magnetic spacers 50 may be provided that can be swapped out by a patient or health care provider that provide more or less magnetic coupling force.

Figure 9:
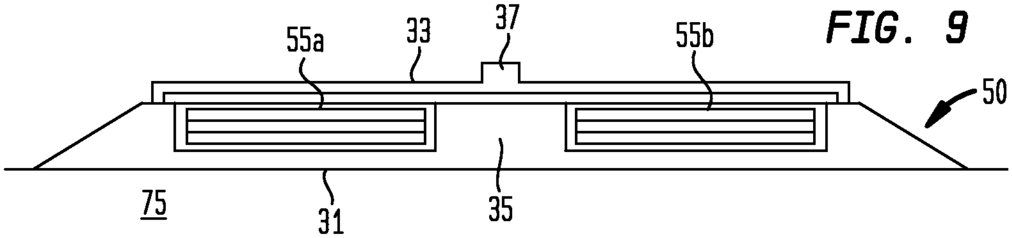

In one embodiment shown in FIG. 9, a multi-piece magnetic spacer 50 is provided where cap 37 and base 35 have stacks of magnetic members 55*a* and 55*b* disposed therebetween. The thickness of base 35 can be varied by swapping out one base 35 for a different base 35 having a different thickness, thereby changing the amount of magnetic coupling force provided by magnetic spacer 50.

Figure 10:
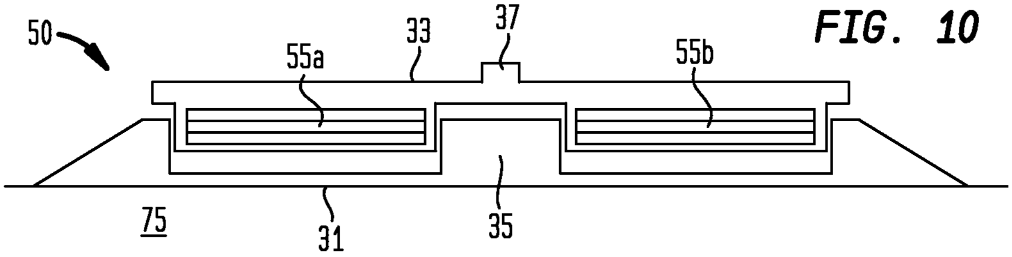

In FIG. 10 there is shown another embodiment of magnetic spacer 50 having cap 37 and 35, where magnetic members 55*a* and 55*b* are contained within cap 37, and where the magnetic coupling force provided by magnetic spacer 50 may be varied by exchanging one cap 37 having a first magnetic coupling force associated therewith for another cap 37 having a second magnetic coupling force associated therewith.

Figure 11:
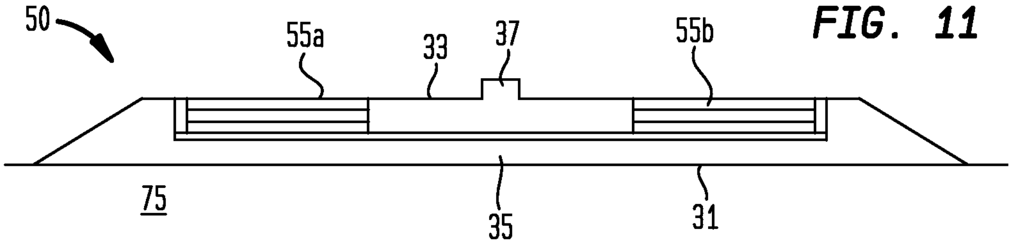

FIG. 11 shows one embodiment of magnetic spacer 50 having cap 37 and base 35, where magnets 55 are contained within cap 37, and where the thickness of base 35 can be varied by exchanging one base 35 having a first thickness associated therewith for another base 35 having a second thickness associated therewith, thereby permitting the thickness of base 35 to be varied, and thus the amount of magnetic coupling force delivered by magnetic spacer 50 to be varied or adjusted.

Figure 12:
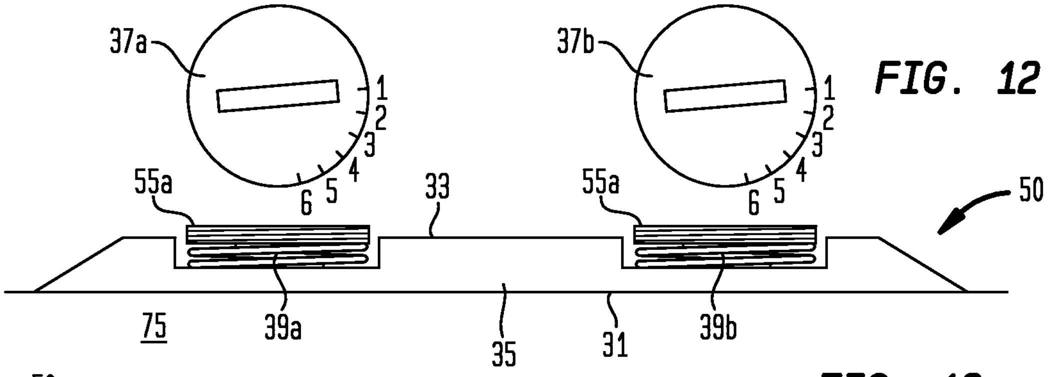

FIG. 12 shows one embodiment of magnetic spacer 50, where magnetic members 55*a* and 55*b* are enclosed within base 35 below threaded lids 37*a* and 37*b* atop springs 39*a* and 39*b*, where threaded lids 37*a* and 37*b* may be turned inwardly or outwardly to compress or decompress springs 39*a* and 39*b* and thereby vary the distance between magnetic members 55*a* and 55*b* and the patients skin 75.

Figure 13:
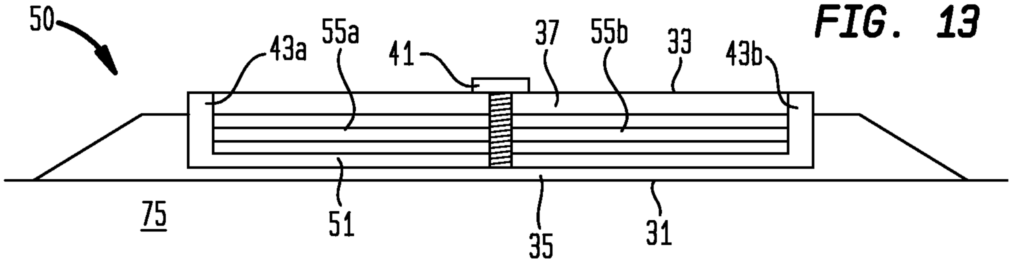

FIG. 13 shows one embodiment of magnetic spacer 50 having magnetic members 55*a* and 55*b* located on moveable plate 51, plate 51 being attached to slideable guide pins 43*a* and 43*b*, where screw 41 is threaded into plate 51 such that turning screw 41 raises or lowers plate 51 on guide pins 43*a* and 43*b*, thereby varying the distance between magnetic members 55*a* and 55*b* and the patient's skin.

Figure 14:
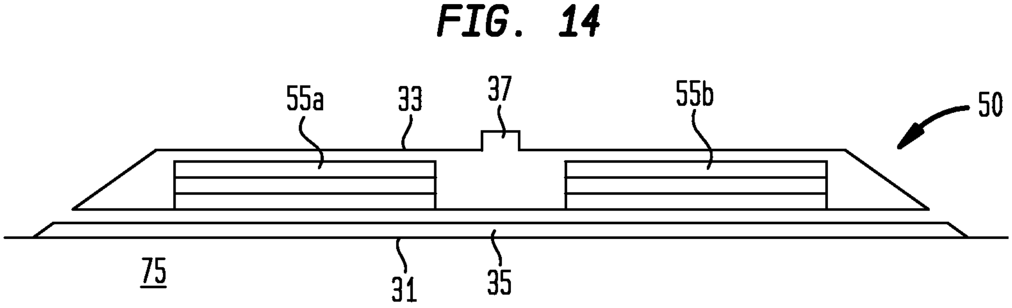

FIG. 14 shows another embodiment of multi-piece magnetic spacer 50 having cap 37 and base 35, where magnets 55 are contained within cap 37, and where the thickness of base 35 can be varied by exchanging one base 35 having a first thickness associated therewith for another base 35 having a second thickness associated therewith, thereby permitting the thickness of base 35 to be varied, and thus the amount of magnetic coupling force delivered by magnetic spacer 50 to be varied or adjusted.

Figure 15:
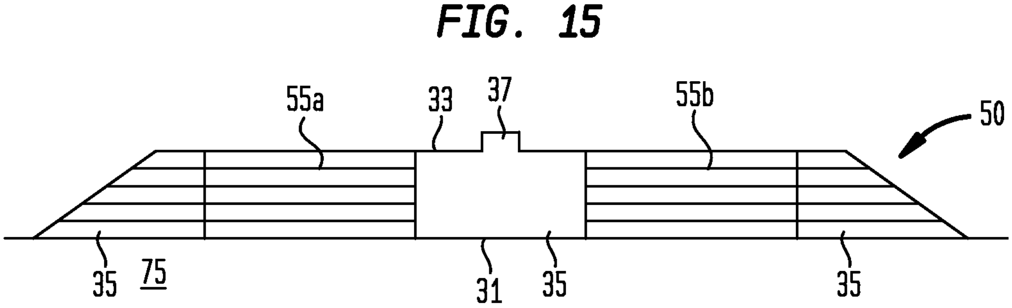

FIG. 15 shows an embodiment of magnetic spacer 50 where multi-piece spacer 50 comprises pairs of stacks of magnets 55*a* and 55*b*, each contained within its own plate, where plates may be swapped out and stacked to achieve different magnetic strengths.

Figure 16:
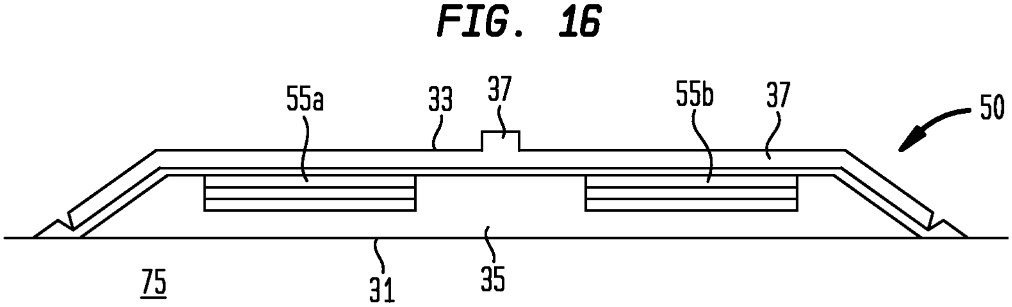

FIG. 16 shows one embodiment where variations in thickness are provided by different color caps 37 and corresponding bases, where each color magnetic spacer 50 has a predetermined magnetic coupling force associated therewith. The patient or health care provider thus selects a magnetic spacer 50 having the desired amount of magnetic coupling force. In such an embodiment, the thicknesses of bases 35 and the amount of magnetic coupling force provided by magnetic members 55*a* and 55*b* can be varied to provide color-coded magnetic spacers 50 having varying predetermined amounts of magnetic coupling force.

Figure 17:
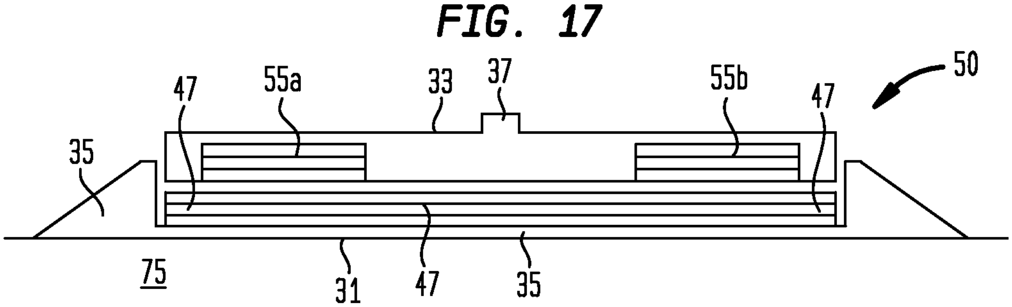

FIG. 17 shows one embodiment where multi-piece magnetic spacer 50 comprises cap 37 and base 35, and where magnet members 55*a* and 55*b* are contained within cap 37, and further where shim plates 47 are stacked between cap 37 and base 35 to achieve the desired spacing. In some such embodiments, shim plates 47 are formed of a non-magnetic material such as a non-ferrous metal, plastic or polymer. In other embodiments, shim plates 47 are divided into two sections corresponding to overlying magnetic members 55*a* and 55*b*, where each such section is magnetic and may be configured to further tune or adjust the amount of magnetic coupling force provided by magnetic spacer 50 in conjunction with the amount of magnetic coupling force provided by magnetic members 55*a* and 55*b*.

For the best sound transmission between audio processor 10 and skull 75, magnetic spacer 50 should have good contact with patient's skin 70. However, if magnetic spacer 50 and skin 75 do not have the same corresponding contours, unwanted pressure points and abrasion between skin 75 and magnetic spacer 50 can cause sore spots on the patient's skin. This problem is solved by the embodiments illustrated in FIGS. 18 and 19, where two embodiments of magnetic spacers 50 having conformable and/or custom-contoured layers 52 attached to a lower portion thereof are shown, and where layers 52 are configured to conform to the shape of a patient's head in the region above magnetic implant 20 in skull 70.

Figure 18:
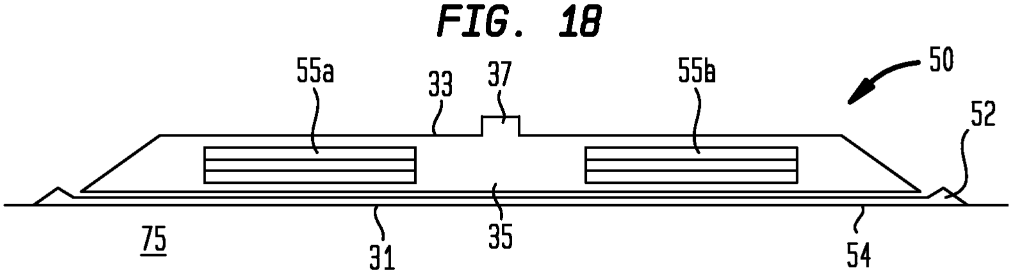

Referring now to FIG. 18, there is shown one embodiment of magnetic spacer 50 where conformable or custom-contoured spacer 52 is provided to operate in conjunction with magnetic spacer 50. In FIG. 18, spacer 52 is disposed between the bottom surface 31 magnetic spacer 50 and skin 75, and is configured to form a pliable or rigid membrane or layer. A portion of the space provided by spacer 52 may be occupied by a small granular substance or powder, a gel, air, a gas, a fluid or a malleable or pliable material such as a suitable flexible polymer. In some embodiments such materials are configured to conform to the patient's anatomy when typical magnetic retention forces are applied, and may further be configured to provide sufficient density and mechanical rigidity to effect a suitable degree of mechanical coupling for vibration transfer from the main body of magnetic spacer 50 to patient's skull 70.

In one embodiment, layer 52 comprises a soft or compliant material that conforms to the patient's head and is then configured to cure or harden according to the contours of the patient's skin 75 and skull 70 after being placed in position. Various hardening methods are available, including hardening mediated via one or more of temperature, oxygen, UV radiation, light, polymerization or polymeric reaction, and two-part epoxies. Alternatively, layer 52 may comprise two or more materials with one such material being configured to conform to the patient's head and being curable as discussed above. Layer 52 may also comprise one or more flexible or hinged plates.

In still other embodiments, and continuing to refer to FIG. 18, a foil, film or layer 52 having a predetermined thickness (e.g., 1-3 mm thickness) forms a portion of the footprint outline or bottom membrane of spacer 50. Layer 52 may be pre-assembled to adhere to bottom 31 of magnetic spacer 50. A protective tape may also be placed over the film and peeled off when spacer 50 is ready to be used. Magnetic spacer 50 is then placed onto skull 70 of the patient, where it is held in place by magnetic coupling forces, and where layer 52 conforms to the patient's anatomy and deforms plastically with respect to the contour of the skull surface. In one such embodiment, layer 52 is configured to harden and cure during a fitting session with the patient, preferably within minutes. Such a layer may comprise, by way of example, two foils or membranes, where each foil or membrane is one of two components of a two-component curable biocompatible epoxy. Air-curable or UV-curable polymers may also be used to form layer 52. Such layers 52 may be configured to eliminate the typical 1-3 mm unevenness in the contours of skull 75 that typically occurs in the vicinity of magnetic implant 20, and thereby provide improved sound transmission and fewer issues with pressure points. Such layers 52 may also comprise gelled films or bandages.

Figure 19:
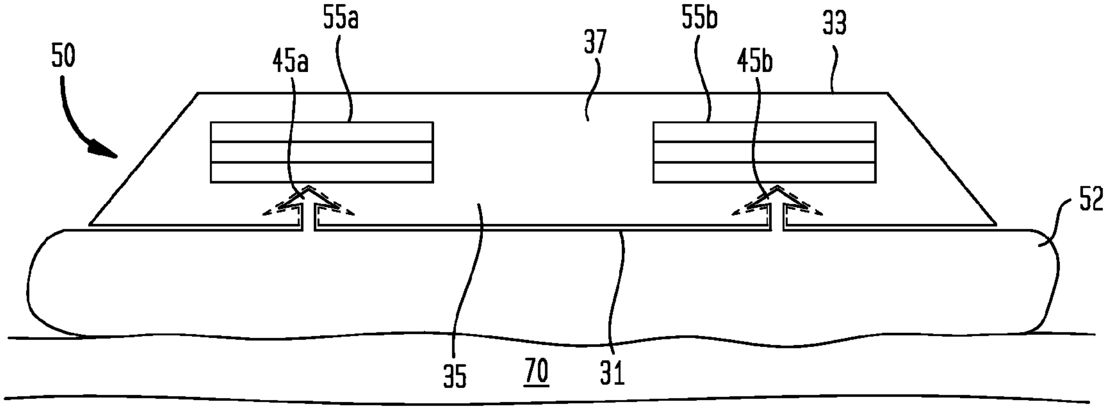

In the embodiment shown in FIG. 19, magnetic spacer 50 comprises a flexible bag or balloon 52 on the bottom, which may be filled to various degrees or amounts using different materials and/or types of materials to vary the spacing, as described above. In the embodiment shown in FIG. 19, layer 52 is secured to magnetic spacer 50 by means of barbs 45*a* and 45*b*, although many other means of securing or affixing layer 52 to magnetic spacer 50 are contemplated, such as adhesives, screws, magnetic coupling, and so on.

According to some embodiments, magnetic members 55*a* and 55*b* are substantially disc-shaped, although other shapes are contemplated. Illustrative diameters of magnetic members 55*a* and 55*b* can range, by way of non-limiting example, between about 8 mm and about 20 mm, and can have thicknesses ranging between about 1 mm and about 4 mm. The center-to-center spacing of magnetic members 55*a* and 55*b* in magnetic spacer 50 may range, by way of non-limiting example, between about 1.5 cm and about 2.5 cm, with a preferred spacing of about 2 cm. Rare earth magnets comprising, by way of example, neodymium, may be employed to provide sufficient amounts of magnetic coupling forces for magnetic members 55*a* and 55*b*. Suppliers of suitable magnetic members 55*a* and 55*b* include K&J Magnetics of Jamison, Pa. and Schallenkammer Magnetsysteme of Rimpar, Germany.

A system adhesion force, or magnetic pull or coupling force, accomplished with magnetic members 55*a* and 55*b* and a corresponding pair of implanted magnets 60*a* and 60*b* located in magnetic implant 20 may range, by way of non-limiting example, between about 0.5 Newtons and about 3 Newtons, with a preferred range of 1. Newton to 2.5 Newtons. As described above, variability in such an adhesion force can be accomplished with thicknesses of portions of magnetic spacer 50 or with different types and configurations of magnetic members 55*a* and 55*b*, as magnetic members 60*a* and 60*b* have a fixed adhesion force associated therewith once they have been implanted.

Note that the various embodiments of magnetic spacers 50 are not limited to embodiments having only two magnetic members 55*a* and 55*b*, or two stacks of magnetic members 55*a* and 55*b*. Instead, more than two magnetic members 55*a* and 55*b* may be employed in magnetic spacer 50, as described in the above-referenced patent application entitled "Adjustable Magnetic Systems, Devices, Components and Methods for Bone Conduction Hearing Aids." Note further that many of the various embodiments of magnetic spacers 50 disclosed in the foregoing patent application may be modified in accordance with the teachings presented herein to provide magnetic spacers 50 having the desired amount, orientation and direction of magnetic coupling force that is appropriate or optimal for a given patient. Thus, those skilled in the art will now understand that many different permutations, combinations and variations of magnetic spacer 50 fall within the scope of the various embodiments.

See also, for example, U.S. Pat. No. 7,021,676 to Westerkull entitled "Connector System," U.S. Pat. No. 7,065,223 to Westerkull entitled "Hearing-Aid Interconnection System," and U.S. Design Pat. No. D596,925 S to Hedstrom et al., which disclose bone screws, abutments and hearing aids that may be modified in accordance with the teachings and disclosure made herein, each of which is hereby incorporated by reference herein, each in its respective entirety.

The above-described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

We claim:

1. A magnetic hearing device, comprising:

at least one housing;

an electromagnetic ("EM") transducer disposed within or attached to the housing; and an adjustable magnetic spacer comprising at least a first magnetic member, the magnetic spacer being configured to be: (i) mechanically and acoustically coupled to the EM transducer, and (ii) magnetically and transcutaneously coupled to an implantable member through a patient's skin, the implantable member being configured to be disposed beneath the patients skin and configured to be attached to the patient's skull;

wherein the adjustable magnetic spacer is further configured such that at least one of:

(a) a user may remove and replace the first magnetic member from the adjustable magnetic spacer;

(b) the user may add or remove at least a second magnetic member to or from the adjustable magnetic spacer;

(c) the user may remove the adjustable magnetic spacer from the device and replace it with a different magnetic spacer or with changes to the adjustable magnetic spacer;

(d) the user may adjust a position of the first magnetic member in the adjustable magnetic spacer so as to change or adjust a degree of magnetic coupling of the adjustable magnetic spacer to the implantable member;

(e) the user may adjust a position of the first magnetic member so as to change or adjust relative positioning or spacing between the adjustable magnetic spacer and the implantable member;

(f) at least a first portion of the adjustable magnetic spacer is custom-shaped to conform with skull contours underlying a desired skin contact region of a given patient;

(g) at least a second portion of the adjustable magnetic spacer is configured to be conformable with skull contours underlying the desired skin contact region of the given patient, and (h) at least portions of the first magnetic member are shaped and configured for placement near a periphery of the adjustable magnetic spacer so as to permit a reduction in a thickness of the magnetic spacer between at least portions of the EM transducer and the patients skin;

and further wherein an adhesion force to the implantable member provided by the adjustable magnetic spacer ranges between about 0.5 Newtons and about 3 Newtons, and the adjustable magnetic spacer permits the magnetic hearing device to be positioned comfortably on a chronic basis on the patient's skull.

2. The magnetic hearing device of claim 1, wherein additional magnetic members different from the first and second magnetic members, and having different magnetic strengths, different magnetic coupling capabilities, or different magnetic characteristics, are available for selection by the user for attachment to or insertion in the adjustable magnetic spacer.

3. The magnetic hearing device of claim 1, wherein the adjustable magnetic spacer is configured such that the user can select a number or type of additional magnetic members different from the first and second magnetic members for use in the magnetic spacer, thereby to change or adjust a degree of magnetic coupling of the adjustable magnetic spacer to the implantable member.

4. The magnetic hearing device of claim 1, wherein the adjustable magnetic spacer is configured such that the user can adjust one or more positions of first or second magnetic members within the adjustable magnetic spacer, thereby to change or adjust relative positioning between the adjustable magnetic spacer and the implantable member.

5. The magnetic hearing device of claim 1, wherein additional magnetic members different from the first and second magnetic members, and having at least one of different dimensions, different thicknesses, different softnesses, different hardnesses, different pliabilities, different materials, different shapes, and different contours, are available for selection by the user for attachment to or insertion in the adjustable magnetic spacer.

6. The magnetic hearing device of claim 1, wherein magnetic spacer attachments having at least one of different dimensions, different thicknesses, different softnesses, different hardnesses, different pliabilities, different materials, different contours, different shapes, different magnetic strengths, and different magnetic characteristics, are available for selection by the user for attachment to or insertion in, and removal from, the adjustable magnetic spacer.

7. The magnetic hearing device of claim 1, wherein the adjustable magnetic spacer is configured to be mechanically and acoustically coupled to the EM transducer through an intervening member.

8. The magnetic hearing device of claim 7, wherein the intervening member is a disc.

9. The magnetic hearing device of claim 7, wherein the intervening member is disposed within or on the adjustable magnetic spacer, or is attached thereto.

10. The magnetic hearing device of claim 1, wherein the first portion of the adjustable magnetic spacer is custom-shaped to conform with skull contours underlying the desired skin contact region of the given patient, and the first portion is also configured for engagement with the given patient's skin or hair.

11. The magnetic hearing device of claim 1, wherein the second portion of the adjustable magnetic spacer is conformable with skull contours underlying the desired skin contact region of the given patient, and the second portion is also configured for engagement with the given patient's skin or hair.

12. The magnetic hearing device of claim 1, wherein the second portion of the adjustable magnetic spacer is conformable with skull contours underlying the desired skin contact region of the given patient, and the second portion is also configured to cure or harden along the such skull contours after being placed in engagement with the given patients skin or hair in a desired location.

13. The magnetic hearing device of claim 1, wherein the first magnetic members of the adjustable magnetic spacer has a diameter ranging between about 8 mm and about 20 mm.

14. The magnetic hearing device of claim 1, wherein the first magnetic member of the adjustable magnetic spacer has a thickness ranging between about 1 mm and about 4 mm.

15. The magnetic hearing device of claim 1, wherein the adhesion force provided by the adjustable magnetic spacer ranges between about 1 Newton to about 2.5 Newtons.

16. The magnetic hearing device of claim 1, wherein the first magnetic member comprises a stack of magnetic members.

17. The magnetic hearing device of claim 1, wherein the device includes a third magnetic member spaced apart from the first magnetic member, and further wherein a center-to-center spacing of the first and third magnetic members ranges between about 1.5 cm and about 2.5 cm.

18. An adjustable magnetic spacer configured for use in conjunction with a magnetic hearing device, the magnetic hearing device comprising at least one housing and an electromagnetic ("EM") transducer disposed within or attached to the housing, the adjustable magnetic spacer comprising at least a first magnetic member, the adjustable magnetic spacer being configured to be: (i) mechanically and acoustically coupled to the EM transducer, and (ii) magnetically and transcutaneously coupled to an implantable member through a patient's skin, the implantable member being configured to be disposed beneath the patients skin, wherein the adjustable magnetic spacer is further configured such that at least one of:

(a) a user or health care provider may remove and replace the first magnetic member from the adjustable magnetic spacer;

(b) the user or health care provider may add or remove at least a second magnetic member to the adjustable magnetic spacer;

(c) the user or health care provider may remove the adjustable magnetic spacer from the device and replace it with a different magnetic spacer or with changes to the adjustable magnetic spacer;

(d) the user or health care provider may adjust a position of the first magnetic member in the magnetic spacer so as to change or adjust a degree of magnetic coupling of the adjustable magnetic spacer to the implantable member;

(e) the user or health care provider can adjust a position of the first magnetic member so as to change or adjust relative positioning or spacing between the adjustable magnetic spacer and the implantable member;

(f) at least a first portion of the adjustable magnetic spacer is custom shaped to conform with skull contours underlying a desired skin contact region of a given patient;

(g) at least a second portion of the adjustable magnetic spacer is configured to be conformable with skull contours underlying the desired skin contact region of the given patient; and (h) at least portions of the first magnetic member are shaped and configured for placement near a periphery of the adjustable magnetic spacer so as to permit a reduction in a thickness of the magnetic spacer between at least portions of the EM transducer and the patient's skin;

and further wherein an adhesion force to the implantable member provided by the adjustable magnetic spacer ranges between about 0.5 Newtons and about 3 Newtons, and the adjustable magnetic spacer permits the magnetic hearing device to be positioned comfortably on a chronic basis on the patient's skull.

19. The adjustable magnetic spacer of claim 18, wherein additional magnetic members different from the first and second magnetic members, and having different magnetic strengths, different magnetic coupling capabilities, or different magnetic characteristics, are available for selection by the user or health care provider for attachment to or insertion in the adjustable magnetic spacer.

20. The adjustable magnetic spacer of claim 18, wherein additional magnetic members different from the first and second magnetic members and configured to permit a degree of magnetic coupling of the adjustable magnetic spacer to the implantable member to be adjusted or changed, are available for selection by the user or health care provider for attachment to or insertion in the adjustable magnetic spacer.

21. The adjustable magnetic spacer of claim 18, wherein additional magnetic members different from the first and second magnetic members and configured such that the user or health care provider can adjust one or more positions of the additional magnetic members within the magnetic spacer thereby to change or adjust relative positioning between the magnetic spacer and the implantable member, are available for selection by the user or health care provider for attachment to or insertion in the adjustable magnetic spacer.

22. The adjustable magnetic spacer of claim 18, wherein a plurality of magnetic spacers of at least one of different dimensions, different thicknesses, different softnesses, different hardnesses, different pliabilities, different materials, different shapes, and different contours are available for selection by the user or health care provider for attachment to or insertion in the magnetic hearing device.

23. The adjustable magnetic spacer of claim 18, wherein magnetic spacer attachments having at least one of different dimensions, different thicknesses, different softnesses, different hardnesses, different pliabilities, different materials, different contours, different shapes, different magnetic strengths, and different magnetic characteristics are available for selection by the user or health care provider for attachment to or insertion in, and removal from, the magnetic spacer.

24. The adjustable magnetic spacer of claim 18, wherein the magnetic spacer is configured to be mechanically and acoustically coupled to the EM transducer through an intervening member.

25. The adjustable magnetic spacer of claim 24, wherein the intervening member is a disc.

26. The adjustable magnetic spacer of claim 24, wherein the intervening member is disposed within or on the adjustable magnetic spacer, or is attached thereto.

27. The adjustable magnetic spacer of claim 18, wherein the first portion of the adjustable is custom-shaped to conform with skull contours underlying the desired skin contact region of the given patient, and the first portion is also configured for engagement with the given patient's skin or hair.

28. The adjustable magnetic spacer of claim 27, wherein the second portion of the adjustable magnetic spacer is conformable with skull contours underlying the desired skin contact region of the given patient, and the second portion is also configured for engagement with the given patient's skin or hair.

29. The adjustable magnetic spacer of claim 27, wherein the second portion of the adjustable magnetic spacer is conformable with skull contours underlying the desired skin contact region of the given patient, and the second portion is also configured to cure or harden along such skull contours after being placed in engagement with the given patient's skin or hair in a desired location.

30. The adjustable magnetic spacer of claim 18, wherein the first magnetic member has a diameter ranging between about 8 mm and about 20 mm.

31. The adjustable magnetic spacer of claim 18, wherein the first magnetic member has a thicknesses ranging between about 1 mm and about 4 mm.

32. The adjustable magnetic spacer of claim 18, wherein the adhesion force provided by the magnetic spacer ranges between about 1 Newton to about 2.5 Newtons.

33. The adjustable magnetic spacer of claim 18, wherein the first magnetic member comprises a stack of magnetic members.

34. The adjustable magnetic spacer of claim 18, wherein the device includes a third magnetic member spaced apart from the first magnetic member, and further wherein a center-to-center spacing of the first and third magnetic members ranges between about 1.5 cm and about 2.5 cm.

35. A method of adjusting a fit or coupling of a magnetic hearing device to a patient's head, the device comprising at least one housing, an electromagnetic ("EM") transducer disposed within or attached to the housing, and an adjustable magnetic spacer comprising at least a first magnetic member, the adjustable magnetic spacer being configured to be mechanically and acoustically coupled to the EM transducer, and further being configured to be magnetically and transcutaneously coupled to an implantable member through the patient's skin, the implantable member being disposed beneath the patient's skin and attached to the patient's skull, the method comprising a user or health care provider determining desired settings for the adjustable magnetic spacer by carrying out at least one of the following steps:

(a) a user or health care provider removing and replacing the adjustable magnetic member from the magnetic spacer;

(b) the user or health care provider adding or removing at least a second magnetic member to the adjustable magnetic spacer;

(c) the user or health care provider removing the adjustable magnetic spacer from the device and replacing it with a different magnetic spacer or with changes to the adjustable magnetic spacer;

(d) the user or health care provider adjusting a position of the first magnetic member in the adjustable magnetic spacer so as to change or adjust a degree of magnetic coupling of the adjustable magnetic spacer to the implantable member;

(e) the user or health care provider adjusting a position of the first magnetic member so as to change or adjust relative positioning or spacing between the adjustable magnetic spacer and the implantable member, and (f) conforming at least a first portion of the adjustable magnetic spacer with skull contours underlying a desired skin contact region of a given patient;

wherein an adhesion force to the implantable member provided by the adjustable magnetic spacer ranges between about 0.5 Newtons and about 3 Newtons, and the adjustable magnetic spacer permits the magnetic hearing device to be positioned comfortably on a chronic basis on the patient's skull.

36. The method of claim 35, further comprising selecting the first magnetic member from among a plurality of magnetic members having at least one of different magnetic strengths, different magnetic coupling capabilities, and different magnetic characteristics.

37. The method of claim 35, further comprising selecting the first magnetic member from among a plurality of magnetic members thereby to change or adjust a degree of magnetic coupling of the magnetic spacer to the implantable member.

38. The method of claim 35, further comprising adjusting one or more positions of the first magnetic member to change or adjust relative positioning between the magnetic spacer and the implantable member.

39. The method of claim 35, further comprising selecting the first magnetic spacer from among a plurality of magnetic spacers having at least one of different dimensions, different thicknesses, different softnesses, different hardnesses, different pliabilities, different materials, different shapes, and different contours.

40. The method of claim 35, further comprising selecting a magnetic spacer attachment from among a plurality of magnetic spacer attachments having at least one of different dimensions, different thicknesses, different softnesses, different hardnesses, different pliabilities, different materials, different contours, different shapes, different magnetic strengths, and different magnetic characteristics.

41. The method of claim 35, wherein conforming at least a first portion of the adjustable magnetic spacer with skull contours underlying a desired skin contact region of a given patient further comprises curing or hardening the first portion along the skull contours.

* * * * *